United States Patent [19]

Blaha et al.

[11] Patent Number: 4,765,336

[45] Date of Patent: Aug. 23, 1988

[54] SUPPLEMENT ARRANGEMENT FOR A SLIT-LAMP APPARATUS FOR TREATING THE EYE BY MEANS OF LASER RAYS

[75] Inventors: Erich Blaha, Essingen; Hartmut Gärtner, Oberkochen, both of Fed. Rep. of Germany

[73] Assignee: Carl-Zeiss-Stiftung, Heidenheim, Fed. Rep. of Germany

[21] Appl. No.: 4,544

[22] Filed: Jan. 16, 1987

[30] Foreign Application Priority Data

Jan. 20, 1986 [DE] Fed. Rep. of Germany ....... 8601287

[51] Int. Cl.$^4$ ............................................ A61B 17/36
[52] U.S. Cl. .................................................. 128/395
[58] Field of Search .................... 128/303.1, 395–398; 219/121 LQ, 121 LR, 121 LU

[56] References Cited

U.S. PATENT DOCUMENTS

| 3,096,767 | 7/1963 | Gresser et al. | 128/395 |
| 3,783,874 | 1/1974 | Koester et al. | 128/303.1 |
| 4,164,222 | 8/1979 | Prokhorov et al. | 128/303.1 |
| 4,289,378 | 9/1981 | Remy et al. | 128/395 |
| 4,397,310 | 8/1983 | Pomerantzeff | 128/395 |
| 4,409,979 | 10/1983 | Roussel et al. | 128/395 |
| 4,520,816 | 6/1985 | Schachar et al. | 128/395 |
| 4,520,824 | 6/1985 | Swaniger et al. | 128/395 |
| 4,538,608 | 9/1985 | L'Esperance | 128/395 |
| 4,554,917 | 11/1985 | Tagnen | 128/395 |
| 4,644,948 | 2/1987 | Lang et al. | 128/395 |

FOREIGN PATENT DOCUMENTS

| 1276863 | 9/1968 | Fed. Rep. of Germany | 128/395 |
| 2202120 | 7/1973 | Fed. Rep. of Germany | 128/303.1 |
| 0137054 | 8/1979 | Fed. Rep. of Germany | 128/303.1 |

Primary Examiner—Max Hindenburg
Attorney, Agent, or Firm—Walter Ottesen

[57] ABSTRACT

A known slit-lamp apparatus includes a slit projector defining an optical axis and a corneal microscope. A supplement arrangement makes it possible to conduct a laser treatment with the known slit-lamp apparatus. A therapeutic laser beam is reflected coaxially into the projection beam path of the slit projector. An optical displacement arrangement is mounted on the optical axis downstream of where the therapeutic laser beam is reflected in and serves to displace the laser beam and the projection beam horizontally with respect to the optical axis.

6 Claims, 2 Drawing Sheets

SUPPLEMENT ARRANGEMENT FOR A SLIT-LAMP APPARATUS FOR TREATING THE EYE BY MEANS OF LASER RAYS

FIELD OF THE INVENTION

The invention relates to a slit-lamp apparatus which includes a slit projector and a corneal microscope.

BACKGROUND OF THE INVENTION

For treating diseases of the eye, it is known to direct the rays of a laser light source onto the eye of a patient with the use of ophthalmic viewing apparatus. Apparatus for laser treatment of the eye are disclosed, for example, in U.S. Pat. No. 3,720,213. It is a disadvantage of these known apparatus that they are designed as single-purpose devices for laser therapy and therefore the acquisition of a complete, complex apparatus is required for this purpose.

SUMMARY OF THE INVENTION

It is an object of the invention to provide a supplement arrangement for known slit-lamp apparatus which makes it possible to conduct a laser treatment with already available slit-lamp apparatus.

This object is realized with the supplement arrangement according to the invention which is for the slit-lamp apparatus. The slit-lamp apparatus includes a slit projector defining an optical axis and a corneal microscope. The supplement arrangement includes the slit-lamp projector having a collector lens and an objective lens mounted on the optical axis in spaced relationship to each other so as to conjointly define a parallel projection beam path therebetween. A therapeutic laser beam arrangement includes: a laser light source mounted parallel to the optical axis for generating a therapeutic laser beam; first deflection means for deflecting the laser beam 90° into the parallel projection beam path; second deflection means located downstream of said first deflection means and arranged on the optical axis and in the parallel projection beam path for deflecting the laser beam through 90° so as to be on a laser beam path coaxial with the projection beam path. Finally, optical displacement means is arranged on the optical axis and downstream of the second deflection means for displacing the laser beam path and the projection beam path.

In an especially advantageous embodiment of the invention, the therapeutic laser beam is reflected coaxially into the projection beam path of the slit projector and a laser target beam is mirrored coaxially into the viewing beam path of the corneal microscope.

The advantages achieved with the supplement arrangement according to the invention are especially seen in that a retrofit of available slit-lamp apparatus is thereby made possible and that no respectively different excursion distances exist between the slit-illuminating beam path and the laser-therapeutic beam path. This is especially significant for treatment in the peripheral regions of the patient's eye.

BRIEF DESCRIPTION OF THE DRAWING

The invention will now be described with reference to the drawing wherein.

DESCRIPTION OF THE PREFERRED EMBODIMENTS OF THE INVENTION

Figure 1:
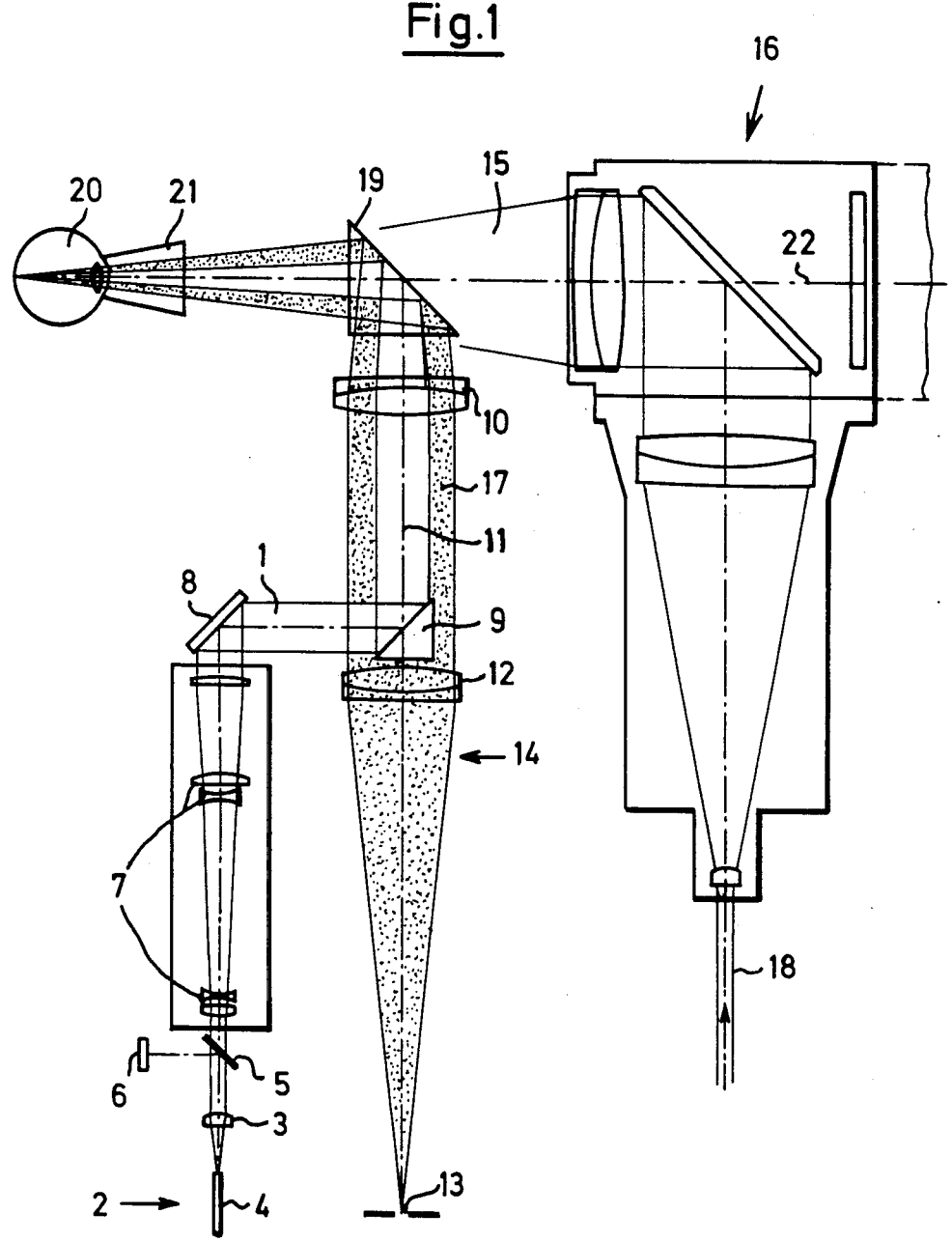
FIG. 1 shows the beam path of the supplement arrangement according to the invention in a slit-lamp apparatus; and, FIG. 2 is a schematic cross-sectional representation of a displacement mechanism for a horizontally displaceable optical element.

In the embodiment according to FIG. 1, the beam 1 of the laser light source 2 passes through a divider plate 5 after passing out from the out-coupling lens 3 of a gradient fiber 4. A small quantity of the laser radiation is reflected at this divider plate and is directed to a measuring diode 6 which is provided for comparison measurement purposes. The beam expansion system 7 makes possible the change of the coagulation field diameter. The coupling into the slit-illuminating beam path occurs via the mirrors 8 and 9. This coupling into the slit-illuminating beam path is without difficulty with respect to the imaging since it occurs in the parallel region of the slit-imaging optics and within the focal length of the objective lens 10. The symmetrical arrangement of the mirror 9 to the optical axis 11 of the slit projector has the consequence that the reflecting surface can be used completely for the deflection of the laser beam and the outer free region of the illuminating beam path can continue to be used completely for the slit illumination.

A further advantage of this geometrical beam division is seen in the independence of the laser wavelength. The focus plane of the laser and viewing beam coincide because of the common imaging of the laser and illuminating beam paths by means of the objective lens 10.

The slit to be imaged on the eye 20 is designated with reference numeral 13. The illuminating beam bundle emanating from the slit 13 is altered by the collective lens 12 so as to be parallel.

A deflecting prism 19 directs the illuminating beam 17 and the laser therapeutic beam 1 arranged coaxially therewith as well as the viewing beam 15 leaving the corneal microscope 16 onto the eye 20. A contact glass 21 is mounted in front of the eye 20.

A second laser beam 18 is coupled in perpendicular to the optical axis 22 of the corneal microscope 16. This second laser beam 18 is, for example, from a YAG-laser and is utilized as a He-Ne target beam.

Figure 2:
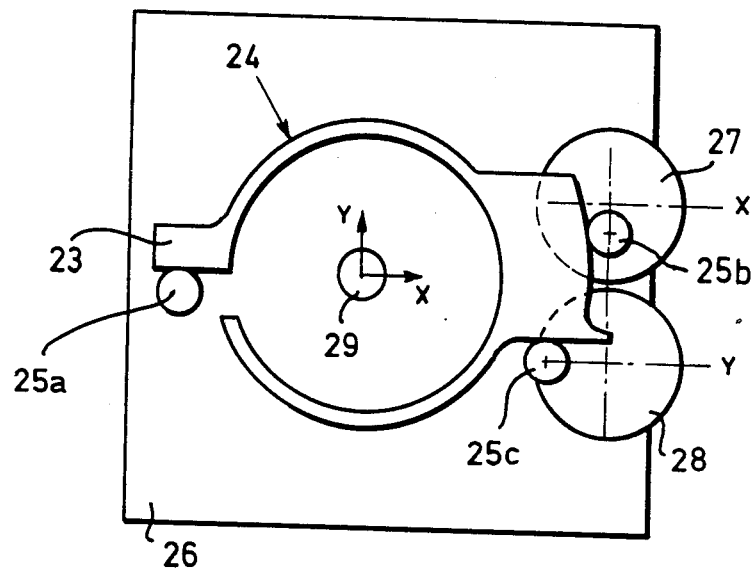

A common, sensitive displacement of the laser and illuminating beam paths onto the retina of the patient with the radial displacement of the objective lens 10 is achieved by means of the displacing mechanism shown in FIG. 2. The bearing bushing 23 carries the objective lens 10 which is to be manipulated and is movably mounted on the housing 26.

A spring 24 presses the bearing bush 23 against three roller bearings (25a, 25b, 25c). The roller bearing 25a is mounted so as to be fixed with respect to the housing; whereas, the roller bearing 25b is connected with the drive wheel 27 for initiating a movement in the X-direction. In the same manner, the roller bearing 25c is connected with the drive wheel 28 and initiates a movement in the Y-direction.

Through simultaneous manipulation of both drives, the bearing bush 23 and therefore the laser and illuminating beam paths can be displaced as desired within the manipulating region 29. For this purpose, the drives can be advantageously motor-driven. Contemplated are also other drive systems such as hydraulic, pneumatic and the like.

This manipulation of the laser and illuminating beam path can also be achieved in an alternate manner by means of a cardanic suspension of the deflecting prism 19. In this case, the objective lens 10 is fixedly mounted.

For reasons of safety, the pivot angle between the lamp housing of the slit illumination and the corneal microscope is limited with mechanical stops in conventional apparatus. This relatively small pivot angle has the consequence that other examining methods such as tonometry cannot be carried out with these apparatus. The use of these apparatus together with a Nd-YAG laser, which has a high aperture, is also not possible.

With the supplement arrangement according to the invention, this disadvantage is avoided by means of an electrical monitoring of the pivot angle between the lamp housing and the corneal microscope. This electrical monitoring functions in such a manner that a switch only releases the laser 1 (for example argon) when the pivot angle is smaller than a predetermined value, for example, ±15°. The switch is mounted in a carrier arm (not shown) of the corneal microscope or in the lamp housing. On the other hand, the laser 2 (for example Nd-YAG) cannot be used under this condition. The use of this laser is only then possible after a predetermined pivot angle (for example, a pivot angle greater than ±15°). Since the illuminating beam path of this arrangement is not influenced, other investigating methods, for example tonometry, continue to be possible without limitation.

It is understood that the foregoing description is that of the preferred embodiments of the invention and that various changes and modifications may be made thereto without departing from the spirit and scope of the invention as defined in the appended claims.

What is claimed is:

1. Supplement arrangement for a slit-lamp apparatus which includes a slit projector defining an optical axis and a corneal microscope, the supplement arrangement comprising:
   the slit projector having a collector lens and an objective lens both mounted on said optical axis in spaced relationship to each other so as to conjointly define a parallel projection beam path therebetween along which a beam having mutually parallel rays is transmitted;
   a therapeutic laser beam arrangement including: a laser light source mounted adjacent said optical axis for generating a therapeutic laser beam; first deflection means for deflecting said laser beam into said projection beam path; second deflection means located downstream of said first deflection means and arranged on said optical axis and in said projection beam path for deflecting said laser beam toward said objective lens so as to be on a laser beam path coaxial with said projection beam path; and,
   displacement means arranged on said optical axis downstream of said second deflection means for displacing said objective lens transversely with respect to said optical axis so as to simultaneously displace only said laser beam path and said projection beam path transversely to said optical axis.

2. The supplement arrangement of claim 1, said displacement means comprising:
   a housing;
   a bearing bushing movably mounted on said housing for carrying said objective lens therein;
   a first drive wheel rotatably mounted on said housing and having a first roller for engaging said bushing to effect a shift thereof in a first direction;
   a second drive wheel rotatably mounted on said housing and having a second roller for engaging said bushing to effect a shift thereof in a second direction;
   a third roller mounted on said housing and engaging said bushing; and,
   resilient biasing means for biasing said bushing so as to be in contact engagement with said rollers.

3. A slit lamp apparatus comprising:
   a slit projector defining an optical axis along which an illuminating beam having mutually parallel rays is projected; said slit projector including: a collector lens and an objective lens both mounted on said optical axis in spaced relationship to each other so as to conjointly define a parallel projection beam path therebetween along which said illuminating beam is transmitted;
   a therapeutic laser beam arrangement including: a laser light source mounted adjacent said optical axis for generating a therapeutic laser beam; first deflection means for deflecting said laser beam into said projection beam path; second deflection means located downstream of said first deflection means and arranged on said optical axis and in said projection beam path for deflecting said laser beam toward said objective lens so as to be on a laser beam path coaxial with said projection beam path;
   a corneal microscope for generating a viewing beam and for defining a viewing beam path;
   optical transmitting and deflecting means arranged downstream of said objective lens and on said viewing beam path for directing said therapeutic laser beam and said illuminating beam into said viewing beam path and for directing all of said beams onto the eye of the patient; and,
   displacement means arranged on said optical axis downstream of said second deflection means for displacing said objective lens transversely with respect to said optical axis so as to simultaneously displace said laser beam path and said projection beam path transversely to said optical axis to thereby effect a displacement only of said laser beam and said illuminating beam on the retina of the patient.

4. The slit lamp apparatus of claim 3, comprising:
   a second laser beam source for generating a target beam; and,
   reflection means for reflecting said target beam into said viewing beam path and toward said optical transmitting and deflecting means.

5. The slit lamp apparatus of claim 3, said second deflection means being a geometrical beam divider covering only the central part of the projection beam path.

6. The slit lamp apparatus of claim 3, said displacement means comprising:
   a housing;
   a bearing bushing movably mounted on said housing for carrying said objective lens therein;
   a first drive wheel rotatably mounted on said housing and having a first roller for engaging said bushing to effect a shift thereof in a first direction;
   a second drive wheel rotatably mounted on said housing and having a second roller for engaging said bushing to effect a shift thereof in a second direction;
   a third roller mounted on said housing and engaging said bushing; and,
   resilient biasing means for biasing said bushing so as to be in contact engagement with said rollers.

* * * * *